(12) United States Patent
Dong et al.

(10) Patent No.: US 11,771,690 B2
(45) Date of Patent: Oct. 3, 2023

(54) SOLID PARTICLE, PREPARATION METHOD THEREFOR, AND PHARMACEUTICAL COMPOSITION CONTAINING SOLID PARTICLE

(71) Applicant: SHANGHAI WD PHARMACEUTICAL CO., LTD, Shanghai (CN)

(72) Inventors: Liang Chang Dong, Shanghai (CN); Wenbo Ma, Shanghai (CN); Lin Wang, Shanghai (CN)

(73) Assignee: SHANGHAI WD PHARMACEUTICAL CO., LTD, Shanghai (CN)

( * ) Notice: Subject to any disclaimer, the term of this patent is extended or adjusted under 35 U.S.C. 154(b) by 51 days.

(21) Appl. No.: 16/960,955

(22) PCT Filed: Nov. 27, 2018

(86) PCT No.: PCT/CN2018/117622
§ 371 (c)(1),
(2) Date: Jul. 9, 2020

(87) PCT Pub. No.: WO2019/137103
PCT Pub. Date: Jul. 18, 2019

(65) Prior Publication Data
US 2020/0368221 A1 Nov. 26, 2020

(30) Foreign Application Priority Data
Jan. 10, 2018 (CN) .......................... 201810023696.8

(51) Int. Cl.
*A61K 31/473* (2006.01)
*A61K 31/18* (2006.01)

(52) U.S. Cl.
CPC ............ *A61K 31/473* (2013.01); *A61K 31/18* (2013.01)

(58) Field of Classification Search
None
See application file for complete search history.

(56) References Cited

U.S. PATENT DOCUMENTS

| | | | | |
|---|---|---|---|---|
| 6,096,338 A | * | 8/2000 | Lacy ..................... | A61K 47/14 514/975 |
| 9,005,608 B2 | | 4/2015 | Dong et al. | |
| 9,622,981 B2 | | 4/2017 | Chattaraj et al. | |
| 2005/0207990 A1 | | 9/2005 | Funke et al. | |
| 2008/0200536 A1 | | 8/2008 | Moon et al. | |
| 2010/0247632 A1 | | 9/2010 | Dong et al. | |
| 2011/0244033 A1 | * | 10/2011 | Van Den Heuvel ...... | A61P 9/00 514/603 |
| 2013/0052263 A1 | | 2/2013 | Fikstad et al. | |
| 2013/0129822 A1 | | 5/2013 | Chattaraj et al. | |
| 2014/0179655 A1 | * | 6/2014 | Hojgaard ............... | A61K 47/12 514/181 |
| 2015/0374826 A1 | * | 12/2015 | Patel ...................... | A61K 47/14 514/178 |
| 2017/0304196 A1 | * | 10/2017 | Okada .................. | A61K 9/2081 |
| 2018/0125979 A1 | * | 5/2018 | Chen ......................... | A61P 5/24 |
| 2020/0215081 A1 | * | 7/2020 | Lee ........................ | A61K 47/08 |

FOREIGN PATENT DOCUMENTS

| | | | |
|---|---|---|---|
| CN | 1984644 A | | 6/2007 |
| CN | 101237891 A | | 8/2008 |
| CN | 102413813 | * | 4/2012 |
| CN | 102413813 A | | 4/2012 |
| CN | 104039311 A | | 9/2014 |
| CN | 102413813 B | | 11/2014 |
| CN | 110013467 A | | 7/2019 |
| EP | 2 468 262 A1 | | 6/2012 |
| WO | 03063835 A1 | | 8/2003 |
| WO | 2010092596 A1 | | 8/2010 |
| WO | WO-2010/111397 A1 | | 9/2010 |
| WO | 2012076516 A1 | | 6/2012 |
| WO | WO-2013/074205 A1 | | 5/2013 |
| WO | 2016114521 A1 | | 7/2016 |
| WO | 2018230504 A1 | | 12/2018 |

OTHER PUBLICATIONS

Kim et al. "Preparation and in Vivo Evaluation of a Dutasteride-Loaded Solid Supersaturable Self-Microemulsifying Drug Delivery System"Int. J. Mol. Sci. 2015, 16, 10821-10833.*
Dalvadi "Systemic development of design of experiments (DoE) optimized self-microemulsifying drug delivery system of Zotepine" Epub May 17, 2017.*
Calcium Hydrogel Phosphate PUBCHEM https://pubchem.ncbi.nlm.nih.gov/compound/Calcium-hydrogen-phosphate.*
Sigma-Aldrich C5135 Kolliphor® EL®.*
First Office Action dated Dec. 13, 2021 issued in Chinese Application No. 201880085921.9, with English translation, 9 pages.
Notice of Reasons for Refusal dated Sep. 14, 2021 issued in JP Application No. 2020-558672, with English translation, 16 pages.
International Search Report dated Feb. 28, 2019 issued in International Application No. PCT/CN2018/117622, with English translation, 10 pages.

(Continued)

Primary Examiner — Danah Al-Awadi
(74) Attorney, Agent, or Firm — FOLEY & LARDNER LLP

(57) ABSTRACT

A solid particle, a preparation method therefor, and a pharmaceutical composition. The solid particle comprises a porous solid particle and a non-aqueous liquid formula. The non-aqueous liquid formula comprises 0.10-4.00 wt % of a hydrophobic active pharmaceutical agent, 28.00-99.90 wt % of a hydrophobic solubilizing solution, 0-70.00 wt % of a non-ionic surfactant, and 0-1.00 wt % of an antioxidant. The hydrophobic solubilizing solution comprises a medium-chain monoglyceride and diglyceride, and/or a propylene glycol fatty acid monoester.

16 Claims, 2 Drawing Sheets

(56) References Cited

OTHER PUBLICATIONS

First Office Action dated Apr. 3, 2020 issued in Chinese Application No. 201810023696.8, with English translation, 12 pages.
U.S. Pharmacopeia Chapter 39 <1174 "Powder Flow">, 5 pages.
Second Office Action dated Oct. 23, 2020 issued in Chinese Application No. 201810023696.8, with English translation, 14 pages.
Written Opinion dated Feb. 28, 2019 issued in International Application No. PCT/CN2018/117622, with English translation, 10 pages.
Extended European Search Report dated Feb. 12, 2021 issued in corresponding European Application No. 18900355.1, 6 pages.
Third Office Action dated May 24, 2021 issued in CN Application No. 201810023696.8, with English translation, 10 pages.
Second Office Action dated May 20, 2022 issued CN Application No. 201880085921.9, with English translation, 5 pages.
Communication pursuant to Article 94(3) EPC dated Jan. 5, 2023 issued in European Patent Application No. 18900355.1, 5 pages.

* cited by examiner

SOLID PARTICLE, PREPARATION METHOD THEREFOR, AND PHARMACEUTICAL COMPOSITION CONTAINING SOLID PARTICLE

The present application is a 371 of PCT/CN2018/117622, filed on Nov. 27, 2018, which claims the priority of Chinese patent application No. CN201810023696.8, filed on Jan. 10th, 2018, the contents of which are incorporated herein by reference in their entireties.

FIELD OF INVENTION

The present invention relates to a solid microparticle, a preparation method therefor and a pharmaceutical composition containing the same.

PRIOR ARTS

Avodart® soft gelatin capsules manufactured by Glaxo Smithkline Pharmaceuticals are used for treating benign prostatic hyperplasia (BPH) of men's enlarged prostate. Avodart®'s active ingredient is dutasteride. Dutasteride is a selective steroid 5α-reductase inhibitor, and 5α-reductase is an endoenzyme that can convert testosterone to DHT. Dutasteride has a chemical name of (5α,17β)-N-{2,5-bis(trifluoromethyl)phenyl}-3-oxo-4-azaandrost-1-ene-17-carboxamide, the empirical formula of which is $C_{27}H_{30}F_6N_2O_2$, molecular weight of which is 528.5, and the structural formula of which is shown as follows:

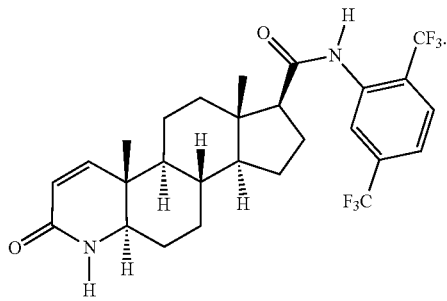

Dutasteride is a white to pale yellow powder with a melting point of 242° C. to 250° C. It is soluble in ethanol (44 mg/mL), methanol (64 mg/mL), and polyethylene glycol 400 (3 mg/mL), but it is insoluble in water.

Hydrophobic active pharmaceutical ingredients (active pharmaceutical agents, APIs), such as dutasteride, have low bioavailability due to their poor solubility in an aqueous medium such as the gastrointestinal tract and solubilization techniques are commonly used to solve this problem. Commercial available Avodart® soft gelatin capsule contains 0.5 mg dutasteride, which is dissolved in a mixture of caprylic/capric mono-/di-glyceride and dibutylhydroxytoluene.

U.S. patent application 20130052263 discloses a formula capable of increasing the solubility of hydrophobic compounds including dutasteride.

The manufacturing process of soft capsules is complicated and with high cost and low efficiency. In addition, soft capsules may be compromised in their integrity or lead to delayed dissolution during storage. The main reason for this phenomenon is the crosslinking and aging of the gelatin of the capsule shells, which forms a large network structure, thereby causing the soft capsule to rely on pepsin environment, otherwise pharmaceutical absorption will be affected. Therefore, U.S. Pat. No. 9,622,981 discloses a liquid-filled hard gelatin capsule formulation that can reduce the manufacturing cost of soft capsules while maintain the bioavailability and stability of the soft gel dosage form. However, the liquid-filled hard capsules require a sealing step to prevent potential liquid leakage during manufacturing and storing period. In addition, the moisture in the hard capsules will migrate to the filled liquid formulation, resulting in a decrease in the moisture content of the hard capsules, which may cause the hard capsules to crack.

U.S. Pat. No. 9,005,608 discloses a formulation for delivering the beneficial medicament Coenzyme Q (CoQ10), and the recrystallisation of dissolved CoQ10 can be prevented by incorporating a supersaturated self-emulsifying formula of CoQ10 into the pores of porous solid particles.

Another commercial product, Jalyn® capsules, manufactured by Glaxo Smithkline Pharmaceuticals, is a pharmaceutical composition of dutasteride and tamsulosin, which can be used for treating benign prostatic hyperplasia (BPH). Tamsulosin is an α1A adrenergic receptor antagonist. Each Jalyn® capsule contains dutasteride soft gelatin capsules and tamsulosin hydrochloride pills, and the capsules and pills are encapsulated in hard shell capsules of #00 size. Although the combined product showed better treatment efficacy than the individual products, the #00 size of Jalyn® capsules reached the maximum value recommended by the FDA. Therefore, they are difficult to be swallowed by BPH patients, especially elderly patients.

Therefore, there is a need for a new oral dosage form that can accommodate the combination of dutasteride and tamsulosin in a hard capsule, which has a size significantly smaller than the Jalyn capsule, and are bioequivalent to Jalyn® capsules.

CONTENT OF THE PRESENT INVENTION

The technical problem to be solved by the present invention is to provide a solid microparticle, a preparation method therefor and a pharmaceutical composition containing the same to overcome the disadvantages of the hydrophobic active pharmaceutical ingredients (active pharmaceutical agents, APIs) in the prior art, such as dutasteride, etc., which have low bioavailability, large dosage form size, poor patient compliance, etc. The solid microparticle can effectively improve solubility of APIs and dissolution rate of medicaments, and can effectively improve the problems of easy cross-linking of soft capsules of commercialized products Avodart® and Jalyn® and oversized dosage form of Jalyn® simultaneously.

The present invention provides a solid microparticle, which comprises porous solid particles and a non-aqueous liquid formula, the non-aqueous liquid formula comprises 0.10% to 4.00% hydrophobic active pharmaceutical ingredient, 28.00% to 99.90% hydrophobic liquid solubilizer, 0 to 70.00% nonionic surfactant, and 0 to 1.00% antioxidant, the percentages refer to the weight percentages accounting for the non-aqueous liquid formula; and the hydrophobic liquid solubilizer comprises medium-chain mono-/di-glyceride, and/or propylene glycol fatty acid monoester.

In the present invention, the content of the hydrophobic active pharmaceutical ingredient may be 0.10% to 2.00% or 0.18% to 2.00%, and the percentages refer to the weight percentages accounting for the non-aqueous liquid formula.

In the present invention, the content of the hydrophobic active pharmaceutical ingredient may be 0.18%, 0.83%, 0.84%, 0.91%, 0.93%, 0.99%, 1.00%, 1.08%, 1.09%, 1.23%, 1.25%, 1.64%, 1.67%, 1.96% or 2.00%, and the percentages refer to the weight percentages accounting for the non-aqueous liquid formula.

In the present invention, the content of the hydrophobic liquid solubilizer may be 32.50% to 99.07%, 39.60% to 99.01%, or 49.50% to 74.26%, and the percentages refer to the weight percentages accounting for the non-aqueous liquid formula.

In the present invention, the content of the hydrophobic liquid solubilizer may be 32.50%, 39.60%, 46.00%, 47.06%, 49.02%, 49.18%, 49.50%, 59.41%, 59.87%, 60.67%, 60.83%, 61.73%, 63.00%, 65.57%, 72.55%, 73.51%, 74.26%, 75.00%, 82.16%, 82.43%, 83.33%, 98.27%, 98.79%, 99.01% or 99.07%, and the percentages refer to the weight percentages accounting for the non-aqueous liquid formula.

In the present invention, when the content of the nonionic surfactant is not 0, the content of the nonionic surfactant may be 15.00% to 66.67%, 24.51% to 59.41%, or 24.75% to 49.50%, and the percentages refer to the weight percentages accounting for the non-aqueous liquid formula.

In the present invention, when the content of the nonionic surfactant is not 0, the content of the nonionic surfactant may be 15.00%, 16.43%, 16.49%, 23.75%, 24.51%, 24.75%, 27.27%, 32.79%, 36.00%, 37.04%, 38.33%, 38.79%, 39.60%, 48.99%, 49.18%, 49.50%, 50.98%, 52.00%, 59.41% or 66.67%, and the percentages refer to the weight percentages accounting for the non-aqueous liquid formula.

In the present invention, when the content of the antioxidant is not 0, the content of the antioxidant may be 0.10% to 1.00% or 0.17% to 0.83%, and the percentages refer to the weight percentages accounting for the non-aqueous liquid formula.

In the present invention, when the content of the antioxidant is not 0, the content of the antioxidant may be 0.17%, 0.28%, 0.33%, 0.51%, 0.83%, or 1.00%, and the percentages refer to the weight percentages accounting for the non-aqueous liquid formula.

In a preferred embodiment of the present invention, the non-aqueous liquid formula comprises 0.10% to 2.00% hydrophobic active pharmaceutical ingredient, 97.00% to 99.80% medium-chain mono-/di-glyceride, and 0.10% to 1.00% antioxidant, and the percentages refer to the weight percentages accounting for the non-aqueous liquid formula.

In a preferred embodiment of the present invention, the non-aqueous liquid formula comprises 0.10% to 4.00% hydrophobic active pharmaceutical ingredient, 95.00% to 99.90% propylene glycol fatty acid monoester, and 0 to 1.00% antioxidant, and the percentages refer to the weight percentages accounting for the non-aqueous liquid formula.

In a preferred embodiment of the present invention, the weight ratio of the porous solid particle to the non-aqueous liquid formula may be a conventional ratio in the art, preferably 2:1 to 3:1, and more preferably 2:1.

In a preferred embodiment of the present invention, the solid microparticle comprises 0.025% to 3.00% hydrophobic active pharmaceutical ingredient, 5.00% to 59.90% hydrophobic liquid solubilizer, and 0 to 45.00% nonionic surfactant, 0 to 0.60% antioxidant, and 40.00% to 75.00% porous solid particle, and the percentages refers to the weight percentages accounting for the solid microparticle.

In the present invention, the content of the hydrophobic active pharmaceutical ingredient may be 0.10% to 2.00%, such as 0.33%, 0.10% or 0.5%, and the percentages refer to the weight percentages accounting for the solid microparticle.

In the present invention, the content of the hydrophobic liquid solubilizer may be 5.00% to 39.90%, 11.50% to 35.00% or 13.20% to 33.00%, and the percentages refer to the weight percentages accounting for the solid microparticle.

In the present invention, the content of the hydrophobic liquid solubilizer may be 11.50%, 12.00%, 13.20%, 15.00%, 16.34%, 16.50%, 20.00%, 24.50%, 24.75%, 25.00%, 30.00%, 31.50%, 33.00%, 35.00%, 35.50%, 35.70%, 36.40%, 36.50% or 39.90%, and the percentages refer to the weight percentages accounting for the solid microparticle.

In the present invention, when the hydrophobic liquid solubilizer is medium-chain mono-/di-glyceride, the content of the hydrophobic active pharmaceutical ingredient is preferably 0.025% to 1.20%, and the content of the medium-chain mono-/di-glyceride is 24.50% to 59.90%, for example, 25.00% or 30.00%, and the percentages refer to the weight percentages accounting for the solid microparticle.

In the present invention, when the hydrophobic liquid solubilizer is propylene glycol fatty acid monoester, the content of the hydrophobic active pharmaceutical ingredient is preferably 0.025% to 2.40%, and the content of the propylene glycol fatty acid monoester is preferably 23.00% to 59.90%, such as 24.50%, 24.75%, 25.00%, 30.00%, 31.50%, 33.00%, 35.00%, 35.50%, 35.70%, 36.40%, 36.50% or 39.90%, and the percentages refer to the weight percentages account for the solid microparticle.

In the present invention, the content of the nonionic surfactant may be 0 to 40.00%. When the content of the nonionic surfactant is not 0, the content of the nonionic surfactant may be 4.50% to 40.00%, 8.17% to 19.80%, or 8.25% to 16.50%, and the percentages refer to the weight percentages accounting for the solid microparticle.

In the present invention, when the content of the nonionic surfactant is not 0, the content of the nonionic surfactant may be 4.50%, 5.00%, 8.17%, 8.25%, 9.50%, 10.00%, 13.00%, 15.00%, 16.33%, 16.50%, 18.00%, 19.80%, 20.00%, 23.00% or 40.00%, and the percentages refer to the weight percentages accounting for the solid microparticle.

In the present invention, when the content of the antioxidant is not 0, the content of the antioxidant may be 0.025% to 0.60%, such as 0.10%, 0.30%, or 0.33%, and the percentages refer to the weight percentages accounting for the solid microparticle.

In the present invention, the content of the porous solid particles may be 40.00% to 75.00% or 60.00% to 70.00%, and the percentages refer to the weight percentages accounting for the solid microparticle.

In the present invention, the content of the porous solid particles may be 40.00%, 40.70%, 45.00%, 49.50%, 50.00%, 59.50%, 60.00%, 63.67%, 64.57%, 64.67%, 66.67%, 69.5%, 69.57%, 69.67%, 70.00%, 74.50% or 75.00%, and the percentages refer to the weight percentages accounting for the solid microparticle.

In the present invention, the content of the non-aqueous liquid formula may be 25.00% to 60.00%, and the percentages refer to the weight percentages accounting for the solid microparticle.

In the present invention, the content of the non-aqueous liquid formula may be 25.00%, 25.50%, 30.00%, 30.33%, 30.43%, 30.50%, 33.33%, 35.33%, 35.43%, 36.33%, 40.00%, 40.50%, 50.00%, 50.50%, 55.00%, 59.30% or 60.00%, and the percentages refer to the weight percentages accounting for the solid microparticle.

In the present invention, the hydrophobic active pharmaceutical ingredient may be one or more than one selected from dutasteride, finasteride, carvedilol, isotretinoin, fentanyl, sufentanil, zaleplon, testosterone, progesterone, hydroxyprogesterone, norprogesterone, norgestrel, chlorothiazide, furosemide, prednisolone, hydrocortisone, betamethasone, danazol, phenytoin, digoxin, dipyridamole, mefenamic acid, griseofulvin, ketoconazole, itraconazole, glibenclamide, and β-carotene, preferably dutasteride.

In the present invention, the medium-chain mono-/di-glyceride refers to an ester chain formed by the esterification of glycerol with one or two $C_6$-$C_{12}$ fatty acids. Commercially available medium-chain mono-/di-glyceride may comprises Capmul@ products manufactured by Abitec.

In the present invention, when the hydrophobic liquid solubilizer comprises medium-chain mono-/di-glyceride, the medium-chain of the medium-chain mono-/di-glyceride is preferably a $C_8$-$C_{10}$ fatty acid chain. The medium-chain mono-/di-glyceride is preferably mono-/di-caprylate/caprate (Capmul MCM), such as caprylic capric mono-/di-glyceride.

In the present invention, the propylene glycol fatty acid monoester refers to an ester chain formed by esterification of propylene glycol with a $C_6$-$C_{12}$ fatty acid.

In the present invention, when the hydrophobic liquid solubilizer comprises propylene glycol fatty acid monoester, the fatty acid of the propylene glycol fatty acid monoester is preferably a $C_8$-$C_{12}$ fatty acid chain. The propylene glycol fatty acid monoester is preferably propylene glycol monolaurate (type II) (LAUROGLYCOL 90) and/or propylene glycol monocaprylate (type II) (CAPRYOL 90), more preferably propylene glycol monocaprylate (type II) (CAPRYOL 90).

In the present invention, the type of the nonionic surfactant is preferably PEGylated type and/or polyol type, and more preferably PEGylated type.

Wherein, the PEGylated nonionic surfactant is preferably polyoxyethylene 35 castor oil (Kolliphor® ELP) and/or caprylocaproyl polyoxylglycerides (LABASOL ALF).

Wherein, polyol type nonionic surfactant is preferably polysorbate 80™.

In the present invention, the antioxidant may be a conventional antioxidant in the art, preferably dibutylhydroxytoluene (BHT) and/or butylhydroxyanisole (BHA), and more preferably dibutylhydroxytoluene (BHT).

In the present invention, the porous solid particles may be a kind of conventional porous carrier in the art, and are preferably one or more than one of calcium hydrogen phosphate (Fujicalin), magnesium aluminometasilicate (Neusilin) and silicon dioxide, and more preferably calcium hydrogen phosphate (Fujicalin).

In the present invention, preferably, the porous solid particles have a specific surface area of >30 m²/g, and adsorb at least 0.40 mL/g the non-aqueous liquid formula, while maintaining flowability simultaneously.

In a preferred embodiment of the present invention, the solid microparticle comprise 0.0025% to 3.00% hydrophobic active pharmaceutical ingredient, 5.00% to 59.90% hydrophobic liquid solubilizer, 0 to 45.00% nonionic surfactant, 0.025% to 0.60% antioxidant, and 40.00% to 75.00% porous solid particles, and the percentages refers to the weight percentages accounting for the solid microparticle.

In a preferred embodiment of the present invention, the solid microparticle comprises 0.33% dutasteride, 33.00% propylene glycol monocaprylate (type II) (CAPRYOL 90), and 66.67% calcium hydrogen phosphate (Fujicalin), and the percentages refers to the weight percentages accounting for the solid microparticle.

In a preferred embodiment of the present invention, the solid microparticle comprises 0.33% dutasteride, 24.75% propylene glycol monocaprylate (type II) (CAPRYOL 90), 8.25% caprylocaproyl polyoxylglycerides (LABASOL ALF), and 66.67% calcium hydrogen phosphate (Fujicalin), and the percentages refers to the weight percentages accounting for the solid microparticle.

In a preferred embodiment of the present invention, the solid microparticle comprises 0.33% dutasteride, 16.5% propylene glycol monocaprylate (type II) (CAPRYOL 90), 16.5% caprylocaproyl polyoxylglycerides (LABASOL ALF), and 66.67% calcium hydrogen phosphate (Fujicalin), and the percentages refers to the weight percentages accounting for the solid microparticle.

In a preferred embodiment of the present invention, the solid microparticle comprises 0.33% dutasteride, 13.2% propylene glycol monocaprylate (type II) (CAPRYOL 90), 19.80% caprylocaproyl polyoxylglycerides (LABASOL ALF) and 66.67% calcium hydrogen phosphate (Fujicalin), and the percentages refers to the weight percentages accounting for the solid microparticle.

In a preferred embodiment of the present invention, the solid microparticle comprises 0.33% dutasteride, 24.75% propylene glycol monocaprylate (type II) (CAPRYOL 90), 8.25% polyoxyethylene 35 castor oil (Kolliphor® ELP), and 66.67% calcium hydrogen phosphate (Fujicalin), and the percentages refers to the weight percentages accounting for the solid microparticle.

In a preferred embodiment of the present invention, the solid microparticle comprises 0.33% dutasteride, 16.50% propylene glycol monocaprylate (type II) (CAPRYOL 90), 16.50% polyoxyethylene 35 castor oil (Kolliphor® ELP), and 66.67% calcium hydrogen phosphate (Fujicalin), and the percentages refers to the weight percentages accounting for the solid microparticle.

In a preferred embodiment of the present invention, the solid microparticle comprises 0.33% dutasteride, 13.20% propylene glycol monocaprylate (type II) (CAPRYOL 90), 19.80% polyoxyethylene 35 castor oil (Kolliphor® ELP), and 66.67% calcium hydrogen phosphate (Fujicalin), and the percentages refers to the weight percentages accounting for the solid microparticle.

In a preferred embodiment of the present invention, the solid microparticle comprises 0.33% dutasteride, 24.50% propylene glycol monocaprylate (type II) (CAPRYOL 90), 8.17% polyoxyethylene 35 castor oil (Kolliphor® ELP), 0.33% dibutylhydroxytoluene (BHT), and 66.67% calcium hydrogen phosphate (Fujicalin), and the percentages refers to the weight percentages accounting for the solid microparticle.

In a preferred embodiment of the present invention, the solid microparticle comprises 0.33% dutasteride, 16.34% propylene glycol monocaprylate (type II) (CAPRYOL 90), 16.33% polyoxyethylene 35 castor oil (Kolliphor® ELP), 0.33% dibutylhydroxytoluene (BHT), and 66.67% calcium hydrogen phosphate (Fujicalin), and the percentages refers to the weight percentages accounting for the solid particle.

The invention also provides a method for preparing the solid microparticle, which comprises the following steps:

(1) mixing the active pharmaceutical ingredient with the hydrophobic liquid solubilizer to obtain a solution when the solid microparticle does not comprise the nonionic surfactant and the antioxidant;

or, mixing the nonionic surfactant and/or the antioxidant, and the active pharmaceutical ingredient and the hydrophobic liquid solubilizer to obtain solution A when the solid particle comprises the nonionic surfactant and/or the antioxidant;

(2) mixing the porous solid particles with the solution obtained in step (1);

or, mixing the porous solid particles with the solution A obtained in step (1).

In step (1), the mixing method may be a conventional mixing method in the art, and is preferably vortexing.

In step (2), the porous solid particles may further comprise a glidant. The glidant may be a conventional glidant in the art, and is preferably silicon dioxide.

The present invention also provides a pharmaceutical composition containing the solid microparticle and tamsulosin.

In the present invention, the pharmaceutical composition may be in a conventional dosage form, such as a hard capsule. The preparation method of the hard capsule can be a conventional preparation method in the art, and specifically, the solid microparticle and tamsulosin are filled into two-piece hard capsules.

In the present invention, the tamsulosin is a commercially available conventional product in the art, for example, it may be tamsulosin sustained-release pellets or tamsulosin hydrochloride sustained-release pellets.

In a preferred embodiment of the present invention, the pharmaceutical composition may also be used in combination, and the solid microparticle in the pharmaceutical composition are preferably dutasteride solid microparticle. The pharmaceutical composition and the tamsulosin sustained-release pellets can be encapsulated in two-piece hard capsules when they are used in combination, and the size of the hard capsule is not greater than #0.

In the present invention, tamsulosin in the pharmaceutical composition can also be replaced with a conventional therapeutic medicament in the art, as long as the therapeutic medicament does not react with the solid microparticle in the present invention and affect the pharmacological activities of the medicament and the solid particle in the present invention.

In the present invention, the term "comprise . . . " may also be expressed as "composed of".

For example, a solid microparticle comprises porous solid particle and a non-aqueous liquid formula. The non-aqueous liquid formula comprises 0.10% to 4.00% hydrophobic active pharmaceutical ingredient, 28.00% to 99.90% hydrophobic liquid solubilizer, and 0 to 70.00% nonionic surfactant, and 0 to 1.00% antioxidant. The percentages refer to the weight percentages, accounting for the non-aqueous liquid formula The hydrophobic liquid solubilizer comprises medium-chain mono-/di-glyceride, and/or propylene glycol fatty acid monoester.

It can also be expressed as that a solid microparticle, which is composed of porous solid particle and a non-aqueous liquid formulation. The non-aqueous liquid formula is composed of 0.10% to 4.00% hydrophobic active pharmaceutical ingredient, 28.00% to 99.90% hydrophobic liquid solubilizer, and 0 to 70.00% nonionic surfactant, and 0 to 1.00% antioxidant. The percentages refer to the weight percentages accounting for the non-aqueous liquid formula. The hydrophobic liquid solubilizer is composed of medium-chain mono-/di-glyceride, and/or propylene glycol fatty acid monoester.

Without violating common knowledge in the art, the above-mentioned various preferred conditions can be optionally combined to obtain preferred embodiments of the present invention.

The reagents and raw materials used in the present invention are all commercially available.

The advantageous effects achieved by the present invention are as follows:

(1) The solid microparticle of the present invention improves the dissolving rate and dissolution of hydrophobic active pharmaceutical ingredients, such as dutasteride. The dutasteride hard capsule formulation prepared by the present invention has a dissolution about 11% to 30% faster than that of commercially available product Avodart® within 0 to 30 minutes.

(2) The solid microparticle of the present invention is made into hard capsules, which can minimize the potential adsorption of hydrophobic active pharmaceutical ingredients, such as dutasteride, on porous solid particles in an aqueous medium with a pH of 3 or more without relying on the pepsin environment.

(3) The method for preparing the hard capsules of the present invention is simple, does not require the use of special equipment, and is suitable for large-scale industrial production. The dutasteride liquid solid microparticle in the present invention can be easily filled into two-piece hard capsules without the requirement of sealing.

Compared with liquid-filled hard gelatin capsules (U.S. Pat. No. 9,622,981), it effectively solves the potential liquid leakage problem of the two-piece hard gelatin capsule sealed with a ribbon-like polymer.

Compared to soft gelatin capsules, the filling volume of the solid microparticle of the present invention is significantly smaller. In addition, the hard capsules of the present invention can also overcome the following disadvantages of soft gelatin capsules, including higher moisture content which is detrimental to moisture-sensitive products, additional impurities generated by migration of plasticizers to the fillers, and the manufacture process including three to seven days of tray drying.

DETAILED DESCRIPTION OF THE PREFERRED EMBODIMENT

Figure 1:
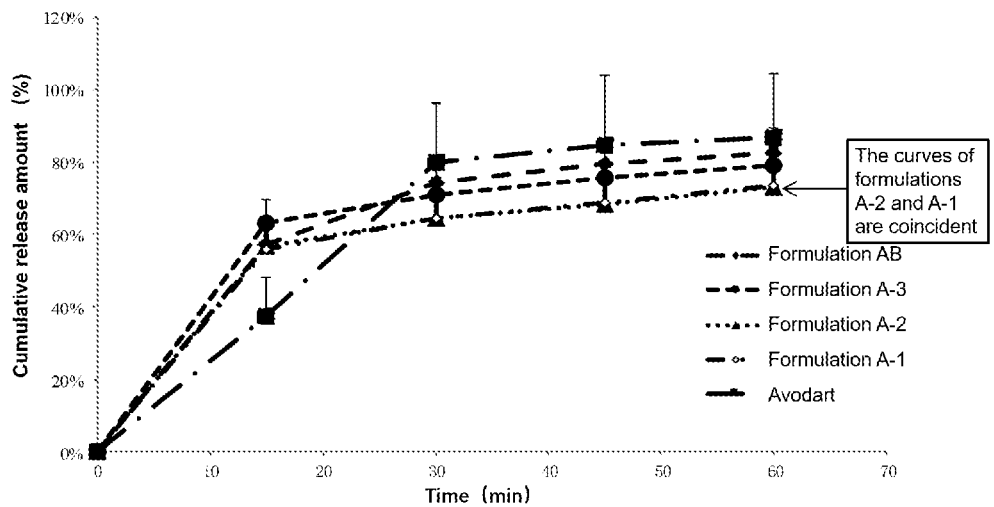
FIG. 1 is a dutasteride dissolution curve figure of each formulation in embodiment 4 and the commercial product Avodart® in a dissolution medium at pH=3.

The present invention is further described by the following embodiments. The present invention is not limited to the scope of the embodiments. The experimental methods without indicating specific conditions are performed under conventional methods and conditions, or according to product specifications.

Embodiment 1

The hydrophobic liquid solubilizers were mixed with Fujicalin at a weight ratio of 2:1, and the flowability of the solid microparticles were estimated by measuring the tap density and bulk density of the solid microparticles.

The compression index (C.I.) and Hausner ratio (H.R.) could be calculated according to the following formula.

$$C.I.=100\times((V_0-V_f)/V_0)$$

$$H.R.=V_0/V_f$$

Wherein $V_0$ and $V_f$ are the bulk density and the tap density of the solid microparticles, respectively.

U.S. Pharmacopeia Chapter 39 <1174 "Powder Flow"> shows the correlation between the powder flowability with the compressibility index and the Hausner ratio (Table 1).

TABLE 1

Flowability and the corresponding compressibility index and Hausner ratio

| Compressibility index (%) | Flowability | Hausner ratio |
| --- | --- | --- |
| ≤10 | Excellent | 1.00-1.11 |
| 11-15 | Good | 1.12-1.18 |
| 16-20 | Fair, no assistance needed | 1.19-1.25 |
| 21-15 | Passable, may shake | 1.26-1.34 |
| 26-31 | Poor-must shake, vibrate | 1.35-1.45 |
| 32-37 | Very poor | 1.46-1.59 |
| >38 | Very, very poor | >1.60 |

The measurement results are shown in Table 2. All hydrophobic liquid solubilizers, including propylene glycol monolaurate (type II) (LAUROGLYCOL 90), propylene glycol monocaprylate (type II) (CAPRYOL 90), caprylic capric mono-/di-glyceride (type I) (Capmul MCM), etc., showed excellent flowability.

TABLE 2

Flowability of the solid microparticles

| No. | Hydrophobic liquid solubilizer | Weight ratio of Fujicalin/non-aqueous liquid formula | Silicon dioxide (%) | Bulk density (g/mL) | Tap density (g/mL) | compressibility index | Hausner ratio |
| --- | --- | --- | --- | --- | --- | --- | --- |
| Embodiment 1-1 | Propylene glycol monolaurate (type II) (LAUROGLYCOL 90) | 2:1 | 0 | 0.685 | 0.748 | 8.50 | 1.09 |
| Embodiment 1-2 | Propylene glycol monocaprylate (type II) (CAPRYOL 90) | 2:1 | 0 | 0.690 | 0.771 | 10.5 | 1.12 |
| Embodiment 1-3 | Caprylic capric mono-/di-glyceride (type I) (Capmul MCM) | 2:1 | 0 | 0.690 | 0.759 | 9.0 | 1.10 |

Embodiment 2

Capryol 90 and Kolliphor® ELP were mixed at a weight ratio of 1:1, mixed with Fujicalin, and then mixed with silicon dioxide at different weight ratios. The flowability of the solid microparticles were estimated by measuring the tap density and the bulk density of the solid.

According to the measurement results shown in Table 3, silicon dioxide-free solid microparticles with a Fujicalin to non-aqueous liquid formula weight ratio of 2:1 or 3:1 had excellent flowability.

TABLE 3

Flowability of the solid microparticles

| No. | Weight ratio of Fujicalin/non-aqueous liquid formula | Silicon dioxide (%) | Bulk density (g/mL) | Tap density (g/mL) | compressibility index | Hausner ratio |
| --- | --- | --- | --- | --- | --- | --- |
| Embodiment 2-1 | 2:1 | 1.0 | 0.629 | 0.718 | 12.5 | 1.14 |
| Embodiment 2-2 | 2:1 | 0.25 | 0.675 | 0.749 | 10.0 | 1.11 |

TABLE 3-continued

Flowability of the solid microparticles

| No. | Weight ratio of Fujicalin/non-aqueous liquid formula | Silicon dioxide (%) | Bulk density (g/mL) | Tap density (g/mL) | compressibility index | Hausner ratio |
|---|---|---|---|---|---|---|
| Embodiment 2-3 | 2:1 | 0 | 0.696 | 0.765 | 9.0 | 1.10 |
| Embodiment 2-4 | 3:1 | 0 | 0.627 | 0.681 | 8.0 | 1.09 |
| Comparative embodiment 1 | 1:0 | 0 | 0.479 | 0.529 | 9.5 | 1.10 |

Embodiment 3

When the solid microparticles were prepared, the content of each component might be as shown in the following table, the percentages referred to the weight percentages accounting for solid microparticles.

TABLE 4

| No. | Hydrophobic active pharmaceutical agent | Hydrophobic liquid solubilizer | Nonionic surfactant | Antioxidant | Porous solid particles |
|---|---|---|---|---|---|
| Embodiment 3-1 | 0.33% dutasteride | 35.00% CAPRYOL 90 | / | / | 64.67% Fujicalin |
| Embodiment 3-2 | 0.33% dutasteride | 35.00% CAPRYOL 90 | / | 0.10% BHT | 64.57% Fujicalin |
| Embodiment 3-3 | 0.33% dutasteride | 35.7% CAPRYOL 90 | / | 0.30% BHT | 63.67% Fujicalin |
| Embodiment 3-4 | 0.33% dutasteride | 35.00% CAPRYOL 90 | / | 0.10% BHT | 34.57% Fujicalin and 30% silicon dioxide |
| Embodiment 3-5 | 0.33% dutasteride | 25.00% CAPRYOL 90 | 5.00% Kolliphor ®ELP | / | 69.67% Fujicalin |
| Embodiment 3-6 | 0.33% dutasteride | 25.00% CAPRYOL 90 | 5.00% LABASOL ALF | / | 69.67% Fujicalin |
| Embodiment 3-7 | 0.33% dutasteride | 25.00% CAPRYOL 90 | 5.00% Polysorbate 80 TM | / | 69.67% Fujicalin |
| Embodiment 3-8 | 0.33% dutasteride | 25.00% CAPRYOL 90 | 5.00% Kolliphor ® ELP | 0.10% BHT | 69.57% Fujicalin |
| Embodiment 3-9 | 0.33% dutasteride | 25.00% CAPRYOL 90 | 5.00% LABASOL ALF | 0.10% BHT | 69.57% Fujicalin |
| Embodiment 3-10 | 0.33% dutasteride | 25.00% CAPRYOL 90 | 5.00% Polysorbate 80 TM | 0.10% BHT | 69.57% Fujicalin |
| Embodiment 3-11 | 0.33% dutasteride | 25.00% CAPRYOL 90 | 5.00% Polysorbate 80 TM | 0.10% BHT | 69.57% Neusilin |
| Embodiment 3-12 | 0.10% dutasteride | 39.90% CAPRYOL 90 | 15.00% Polysorbate 80 TM | / | 45.00% Fujicalin |
| Embodiment 3-13 | 0.50% dutasteride | 20.00% CAPRYOL 90 | 10.00% Polysorbate 80 TM | / | 69.50% Fujicalin |
| Embodiment 3-14 | 0.50% dutasteride | 11.50% CAPRYOL 90 | 13.00% Polysorbate 80 TM | / | 75.00% Fujicalin |
| Embodiment 3-15 | 0.50% dutasteride | 25.00% Capmul MCM | 4.50% Kolliphor ® ELP | / | 70.00% Fujicalin |
| Embodiment 3-16 | 0.50% dutasteride | 12.00% CAPRYOL 90 | 13.00% Kolliphor ® ELP | / | 74.50% Fujicalin |
| Embodiment 3-17 | 0.50% dutasteride | 15.00% CAPRYOL 90 | 15.00% Kolliphor ® ELP | / | 69.50% Fujicalin |
| Embodiment 3-18 | 0.50% dutasteride | 25.00% CAPRYOL 90 | 15.00% Kolliphor ® ELP | / | 59.50% Fujicalin |
| Embodiment | 0.50% | 30.00% | 20.00% | / | 49.50% |

TABLE 4-continued

| No. | Hydrophobic active pharmaceutical agent | Hydrophobic liquid solubilizer | Nonionic surfactant | Antioxidant | Porous solid particles |
|---|---|---|---|---|---|
| 3-19 Embodiment 3-20 | dutasteride 0.50% | CAPRYOL 90 19.50% | Kolliphor ® ELP 40.00% | / | Fujicalin 40.00% |
| Embodiment 3-21 | dutasteride 0.50% | CAPRYOL 90 30.00% | Kollipho ® r ELP 9.50% | / | Fujicalin 60.00% |
| Embodiment 3-22 | dutasteride 0.50% | Capmul MCM 31.50% | Kolliphor ® ELP 18.00% | / | Fujicalin 50.00% |
| Embodiment 3-23 | dutasteride 0.50% | LAUROGLYCOL90 36.50% | LABASOL ALF 23.00% | / | Fujicalin 40.00% |
| Embodiment 3-24 | dutasteride 0.50% | LAUROGLYCOL90 36.40% | LABASOL ALF 23.00% | 0.10% BHT | Fujicalin 40.00% |
| Embodiment 3-25 | dutasteride 0.50% | LAUROGLYCOL90 35.50% | LABASOL ALF 23.00% | 0.30% BHT | Fujicalin 40.70% |

The obtained solid microparticles with dutasteride solid microparticle formulas shown in Table 4 had a Hausner ratio of 1.00 to 1.18 and good flowability.

The obtained solid microparticles with dutasteride solid microparticle formulas shown in Table 4 were made into hard capsule formulations according to the preparation method of embodiment 4, and the dissolution thereof were detected according to the detection method in embodiment 4. They had about the same dissolutions as that of the formulation A-2, and could release about 18% to 25% faster than the reference listed formulation Avodart® within 0-15 minutes.

Embodiment 4

Dutasteride solid microparticle hard capsules were prepared, the formulations of the Dutasteride were shown as follows:

Preparation process of the capsules:
(1) prescribed amounts of dutasteride and CAPRYOL 90 were mixed and vortexed for 5 minutes;
(2) a prescribed amount of surfactant LABASOL ALF was added to obtain a clear solution;
(3) the solution was mixed with porous particles to obtain solid microparticles capable of flowing freely;
(4) 151 mg solid microparticles were filled into #2 hard capsules. Each capsule contained 0.5 mg dutasteride.

Measurement of dissolution:

The obtained hard capsules of each formula in this embodiment and commercially available Avodart® were stirred at 75 rpm according to USP II (paddle method) with 900 mL 0.001N HCl, 1% cetyltrimethylammonium bromide (CTAB) solution as a dissolution medium at a temperature of 37±0.5° C., and sampled at 15 min, 30 min, 45 min, and 60 min. The obtained sample solutions were filtered with a 0.45 μm filter membrane, and quantitatively detected by an HPLC method. The dissolution of dutasteride were calculated. The chromatographic conditions are shown in Table 6, and the dissolution data are shown in FIG. 1.

TABLE 5

Compositions of the hard capsules in embodiment 4

| Component | Formulation AB wt % | Formulation AB wt/capsule mg | Formulation A-1 wt % | Formulation A-1 wt/capsule mg | Formulation A-2 wt % | Formulation A-2 wt/capsule mg | Formulation A-3 wt % | Formulation A-3 wt/capsule mg |
|---|---|---|---|---|---|---|---|---|
| Dutasteride | 0.33 | 0.50 | 0.33 | 0.50 | 0.33 | 0.50 | 0.33 | 0.50 |
| CAPRYOL 90 | 33.00 | 50.00 | 24.75 | 37.50 | 16.50 | 25.00 | 13.20 | 20.00 |
| LABASOL ALF | / | / | 8.25 | 12.50 | 16.50 | 25.00 | 19.80 | 30.00 |
| Fujicalin | 66.67 | 101.00 | 66.67 | 101.00 | 66.67 | 101.00 | 66.67 | 101.00 |
| Total | 100.00 | 151.50 | 100.00 | 151.50 | 100.00 | 151.50 | 100.00 | 151.50 |

TABLE 6

HPLC chromatographic conditions

Instrument
Waters LC aqueous liquid chromatography with automatic sampling, injection and UV detection
Column
Thermo AQUASIL C18 0.46*150 mm, 5 μm
Operation parameters:
Mobile phase: acetonitrile, methanol and water (40:20:35)
Injection volume: 100 μL
Flow rate: 2.0 mL/min
Column temperature: 35° C.
Detector wavelength: UV 240 nm Conclusion: the formulations AB, A-1, A-2 and A-3 of the present invention could release about 18% to 25% faster than the reference listed formulation Avodart® within 0-15 minutes.

Embodiment 5

The formulas of dutasteride formulations are shown as follows:

TABLE 7 compositions of hard capsules in embodiment 5

| / | Formulation B-1 | | Formulation B-2 | | Formulation B-3 | |
|---|---|---|---|---|---|---|
| Component | wt % | wt/capsule mg | wt % | wt/capsule mg | wt % | wt/capsule mg |
| Dutasteride | 0.33 | 0.50 | 0.33 | 0.50 | 0.33 | 0.50 |
| CAPRYOL 90 | 24.75 | 37.50 | 16.50 | 25.00 | 13.20 | 20.00 |
| Kolliphor ® ELP | 8.25 | 12.50 | 16.50 | 25.00 | 19.80 | 30.00 |
| Fujicalin | 66.67 | 101.00 | 66.67 | 101.00 | 66.67 | 101.00 |
| Total | 100.00 | 151.50 | 100.00 | 151.50 | 100.00 | 151.50 |

Figure 2:
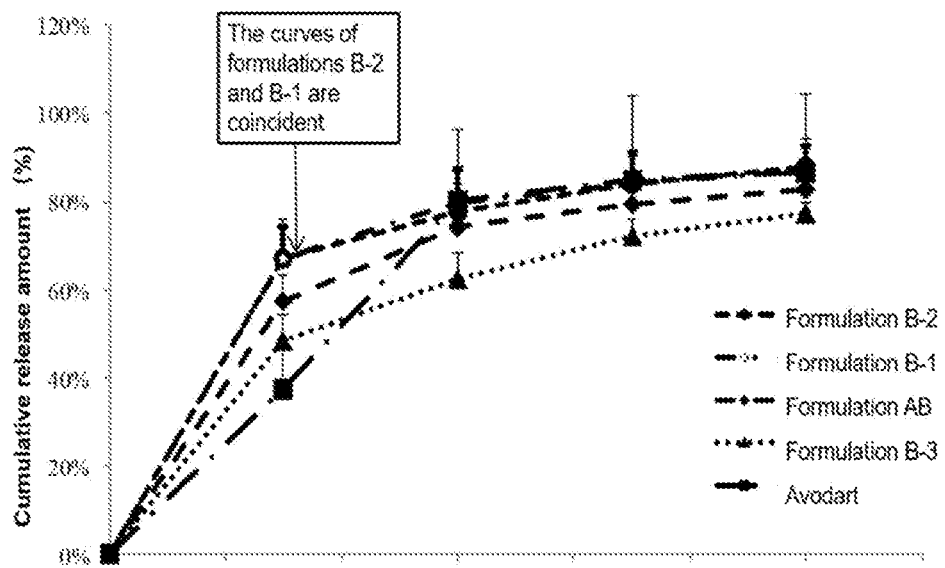
FIG. 2 is a dutasteride dissolution curve figure of each formulation in embodiment 5 and the commercial product Avodart® in a dissolution medium at pH=3.

The preparation process and dissolution rate detection were the same as those in embodiment 4. The dissolution data are shown in FIG. 2.

Conclusions: the formulations B-1, B-2 and B-3 of the present invention could release about 11% to 30% faster than that of the reference listed formulation Avodart® within 0 to 15 min, and the formulations B-1 and B-2 could release a little faster than Avodart® within 0 to 60 min.

Embodiment 6

The formulation B-2 obtained in embodiment 5 and commercially available Avodart® were stirred at 75 rpm according to USP II (paddle method) with 900 mL 0.1N HCl 1% cetyltrimethylammonium bromide (CTAB) solution as a dissolution medium at a temperature of 37±0.5° C. The dissolution medium might or might not contain 0.40% pepsin.

The detection method was the same as that in embodiment 4. The dissolution data are shown in FIGS. 3 and 4.

Figure 3:
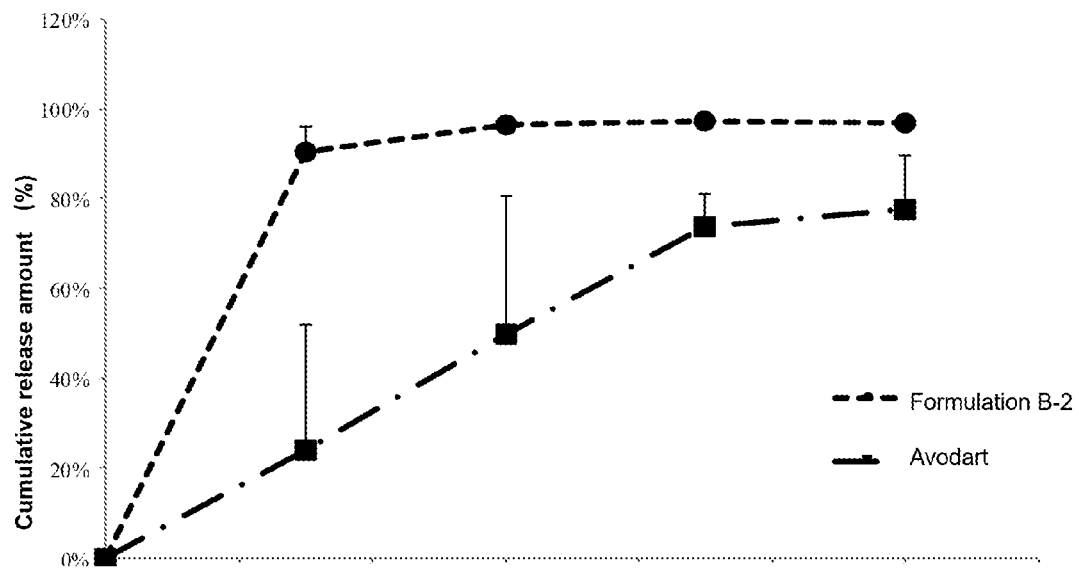
FIG. 3 is a dutasteride dissolution curve figure of formulation in embodiment 6 and the commercial product Avodart® in a dissolution medium without pepsin at pH=1.

Conclusions:

FIG. 3 showed that the formulation B-2 obtained in the embodiment 5 had faster release rate and cumulative dissolution than Avodart® in the dissolution medium without pepsin.

Figure 4:
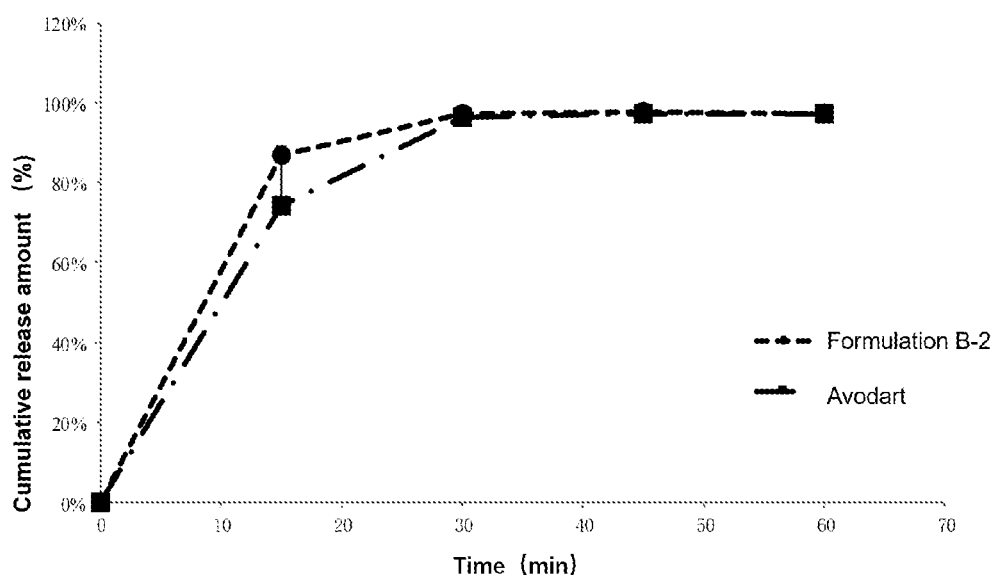
FIG. 4 is a dutasteride dissolution curve figure of formulation in embodiment 6 and the commercial product Avodart® in a dissolution medium containing pepsin at pH=1.

FIG. 4 showed that the formulation B-2 obtained in the embodiment 5 had about the same dissolution curves of hard capsules and soft capsules as those of Avodart® in the dissolution medium containing pepsin.

Compared with Avodart® gelatin soft capsules, dutasteride in the hard capsules of the formulation B-2 showed more consistent dissolution rates without being influenced by the presence of pepsin in the dissolution medium, which might be caused by the potential cross-linking of the Avodart® soft gelatin capsules, resulting in that the dissolution of the medicament depended on pepsin.

Embodiment 7

According to the formula and preparation method of embodiment 5, 171.6 mg tamsulosin sustained-release pills and 150 mg dutasteride solid microparticles (formulation B-2) were prepared and filled together into 0 #hard gelatin capsules. Each capsule contained 0.4 mg tamsulosin and 0.5 mg dutasteride.

Embodiment 8

The formulations of the dutasteride were shown as follows:

TABLE 8

Compositions of hard capsules in embodiment 8

| | Formulation B-4 | | Formulation B-5 | |
|---|---|---|---|---|
| Component | wt % | wt/capsule mg | wt % | wt/capsule mg |
| Dutasteride | 0.33 | 0.50 | 0.33 | 0.50 |
| CAPRYOL 90 | 24.50 | 37.12 | 16.34 | 24.76 |
| Kolliphor ® ELP | 8.17 | 12.38 | 16.33 | 24.74 |
| Fujicalin | 66.67 | 101.00 | 66.67 | 101.00 |
| BHT | 0.33 | 0.50 | 0.33 | 0.50 |
| Total | 100.00 | 151.50 | 100.00 | 151.50 |

The preparation process and detection of dissolution were the same as those in the embodiment 4.

The dissolution data of the formulation B-4 was similar to that of the formulation B-1 in the embodiment 5, and the dissolution data of the formulation B-5 was similar to that of the formulation B-2 in the embodiment 5.

Comparative Embodiment 2

The dutasteride solid microparticle hard capsules were prepared according to the formulas in the table below. The preparation process and detection method were the same as those in the embodiment 4. Captex® 355 are triglycerides of caprylic acid ($C_8$) and capric acid ($C_{10}$).

TABLE 9

| Component | wt % | wt/capsule mg |
|---|---|---|
| Dutasteride | 0.33 | 0.50 |
| CAPRYOL 90 | 24.75 | 37.50 |
| Captex ® 355 | 8.25 | 12.50 |
| Fujicalin | 66.67 | 101.00 |
| Total | 100.00 | 151.50 |

When the hydrophobic liquid solubilizer comprised medium-chain triglycerides, the self-emulsifying property of the prepared dutasteride solid microparticles were significantly lower than that of the dutasteride solid microparticles of the present application, and the dissolution rate thereof was also significantly lower than that of the dutasteride solid microparticles of the present application.

Although the specific embodiments of the present invention are described above, those skilled in the art should understand that these are merely for illustration, and that various changes or modifications may be made to these embodiments without departing from the principle and essence of the present invention. Therefore, the protection scope of the present invention is defined by the appended claims.

What is claimed is:

1. A solid microparticle, which comprises 0.33% hydrophobic active pharmaceutical ingredient, 5.00% to 24.75% hydrophobic liquid solubilizer, 4.50% to 19.80% nonionic surfactant, 0 to 0.60% antioxidant, and 66.67% to 75.00% porous solid particles, wherein the percentages refers to the weight percentages accounting for the solid microparticle; the porous solid particles comprise calcium hydrogen phosphate; the hydrophobic liquid solubilizer comprises propylene glycol monocaprylate type II, propylene glycol monolaurate type II or caprylic capric mono-/di- glyceride type I; and the hydrophobic active pharmaceutical ingredient is dutasteride, wherein the solid microparticle is made into hard capsules and releases dutasteride about 11% to 30% faster than that of dutasteride soft gelatin capsule within 0 to 15 minutes.

2. The solid microparticle as claimed in claim 1, wherein the content of the hydrophobic liquid solubilizer is 11.50% to 24.75%.

3. The solid microparticle as claimed in claim 1, wherein the content of the hydrophobic liquid solubilizer is 13.20% to 24.75%, and the percentages refer to the weight percentages accounting for the solid microparticle.

4. The solid microparticle as claimed in claim 1, wherein the content of the nonionic surfactant is 8.25% to 19.80%, and the percentages refer to the weight percentages accounting for the solid microparticle.

5. The solid microparticle as claimed in claim 1, wherein the content of the nonionic surfactant is 8.25% to 16.50%, and the percentages refer to the weight percentages accounting for the solid microparticle.

6. The solid microparticle as claimed in claim 1, wherein when the content of the antioxidant is not 0, the content of the antioxidant is 0.025% to 0.60%, and the percentages refer to the weight percentages accounting for the solid microparticle.

7. The solid microparticle as claimed in claim 1, wherein the content of the porous solid particles is 66.67% to 70.00%, and the percentages refer to the weight percentages accounting for the solid microparticle.

8. The solid microparticle as claimed in claim 1, wherein, the nonionic surfactant is PEGylated nonionic surfactant or polyol nonionic surfactant.

9. The solid microparticle as claimed in claim 1, wherein the antioxidant is dibutylhydroxytoluene or butylhydroxyanisole.

10. The solid microparticle as claimed in claim 1, wherein the porous solid particles have a specific surface area of >30 $m^2/g$, and adsorb at least 0.40 mL/g the non-aqueous liquid formula while maintaining flowability simultaneously.

11. The solid microparticle as claimed in claim 8, wherein the PEGylated nonionic surfactant is polyoxyethylene 35 castor oil or caprylocaproyl polyoxylglycerides, and the polyol nonionic surfactant is polysorbate 80.

12. The solid microparticle as claimed in claim 8, the nonionic surfactant is PEGylated nonionic surfactant.

13. The solid microparticle as claimed in claim 8, wherein the solid microparticle is selected from any one of the following combinations:

(1) the solid microparticle comprises 24.75% propylene glycol monocaprylate type II, 8.25% caprylocaproyl polyoxylglycerides, and 66.67% calcium hydrogen phosphate;

(2) the solid microparticle comprises 16.50% propylene glycol monocaprylate type II, 16.50% caprylocaproyl polyoxylglycerides, and 66.67% calcium hydrogen phosphate;

(3) the solid microparticle comprises 13.20% propylene glycol monocaprylate type II, 19.80% caprylocaproyl polyoxylglycerides, and 66.67% calcium hydrogen phosphate;

(4) the solid microparticle comprises 24.75% propylene glycol monocaprylate type II, 8.25% polyoxyethylene 35 castor oil, and 66.67% calcium hydrogen phosphate;

(5) the solid microparticle comprises 16.50% propylene glycol monocaprylate type II, 16.50% polyoxyethylene 35 castor oil, and 66.67% calcium hydrogen phosphate;

(6) the solid microparticle comprises 13.20% propylene glycol monocaprylate type II, 19.80% polyoxyethylene 35 castor oil, and 66.67% calcium hydrogen phosphate;

(7) the solid microparticle comprises 24.50% propylene glycol monocaprylate, 8.17% polyoxyethylene 35 castor oil, 0.33% dibutylhydroxytoluene, and 66.67% calcium hydrogen phosphate;

and (8) the solid microparticle comprises 16.34% propylene glycol monocaprylate, 16.33% polyoxyethylene 35 castor oil, 0.33% dibutylhydroxytoluene, and 66.67% calcium hydrogen phosphate, wherein the percentages refer to the weight percentages accounting for the solid particle.

14. A pharmaceutical composition comprising the solid microparticle as claimed in claim 1 and tamsulosin.

15. The pharmaceutical composition as claimed in claim 14, wherein the pharmaceutical composition is in hard capsule form.

16. The pharmaceutical composition as claimed in claim 14, wherein the tamsulosin is tamsulosin sustained-release pellets or tamsulosin hydrochloride sustained-release pellets.

* * * * *